United States Patent [19]

Gurske

[11] Patent Number: 4,696,958

[45] Date of Patent: Sep. 29, 1987

[54] ELECTROPHORETIC TECHNIQUE FOR SEPARATION OF LIPOPROTEINS AND ELECTROPHORETIC GEL FOR USE THEREIN

[75] Inventor: William A. Gurske, Placentia, Calif.

[73] Assignee: Beckman Instruments, Inc., Fullerton, Calif.

[21] Appl. No.: 801,113

[22] Filed: Nov. 22, 1985

[51] Int. Cl.$^4$ .................. C08L 1/00; C08L 3/00; C08L 5/00

[52] U.S. Cl. .................. 524/21; 524/27; 524/28; 524/31; 524/41; 524/55; 524/386

[58] Field of Search .................. 524/21, 27, 28, 31, 524/41, 56, 58, 55, 386

[56] References Cited

U.S. PATENT DOCUMENTS 3,242,120  3/1966  Steuber .................. 524/27
4,453,979  6/1984  DeMasi et al. .................. 424/49

Primary Examiner—John Kight
Assistant Examiner—Nathan M. Nutter
Attorney, Agent, or Firm—William H. May; Arnold Grant; Julia E. Abers

[57] ABSTRACT

An electrophoretic gel which, when used in an electrophoretic process for the separating chylomicrons, beta lipoproteins, pre-beta lipoproteins, and alpha lipoproteins, enables the separation of the alpha lipoprotein band from the faster moving free fatty acid albumin band. The electrophoretic gel comprises a matrix selected from the group consisting of polysaccharides and derivatives thereof, a buffer having a buffering capacity in an alkaline pH range, and an effective amount of a poly(oxyethylene)-poly(oxypropylene)-poly(oxyethylene) block copolymer.

An improved electrophoretic technique characterized in that the above electrophoretic gel is employed therein.

20 Claims, 7 Drawing Figures

ELECTROPHORETIC TECHNIQUE FOR SEPARATION OF LIPOPROTEINS AND ELECTROPHORETIC GEL FOR USE THEREIN

BACKGROUND OF THE INVENTION

1. Field of the Invention

The instant invention pertains to an electrophoretic technique for the separation of lipoproteins and to an electrophoretic gel for use therein.

2. Description of the Prior Art

Electrophoresis involves the placing of a sample substance, such as blood serum or urine, in a support medium across which is maintained a direct current electrical potential. Support media characteristically include paper, agar; agarose; cellulose acetate and polyacrylamide. The electrical potential causes the colloidal particles in the sample substance to migrate toward one or the other electrodes. The amount of migration is determined by the electrical charges on the particles in the sample substance and the magnitude of the imposed electrical potential. Particles with similar properties tend to group into defined areas and thus a determination can be made as to the amount of each class of substance present in the sample. A graph or analog curve of the relative concentrations of particles can provide information as to the relative proportions of each which are contained in the sample substance. These electrophoretograms provide useful information as to blood serum or urine composition which may be used by clinical pathologists or the like.

More particularly, electrophoretic techniques for the separation of lipoproteins and electrophoretic gels for use therein are well known to those skilled in the art. See Bibliography (1-19) In general, electrophoretic gels employed for separating lipoproteins are of the type comprising a matrix selected from the group consisting of a polysaccharide and derivatives thereof. Examples of polysaccharides include, but are not limited to, agar, agarose, and mixtures thereof. Polysaccharide derivatives include, but are not limited to, cellulose acetate. Albumin is often, but not always, incorporated into the gel. In addition, a buffer having a basic pH is also commonly present in these electrophoretic gels. Barbital buffer (pH 8.6) is reported to yield the most satisfactory results.

Due to the great variety of electrophoretic cells and variety of dimensions of gel supporters, the specific electrophoretic conditions vary considerably. In general, electrophoretic conditions are specific for the design of the gel supporters and for the dimension of the cells.

After electrophoretically separating the lipoproteins, the lipoproteins are immobilized in the gel. Typical immobilization methods include fixation and precipitation.

The precipitation technique involves localizing the lipoproteins via the use of a precipitation solution. Numerous precipitation solutions are known to those skilled in the art. If the precipitation technique is employed, the lipoproteins in these gels can then be evaluated by known techniques, e.g., densitometry and integration.

The fixation method involves localizing the lipoprotein via the use of a fixative solution. In this step, one can use any one of the numerous, reported fixative solutions. The gels are then subjected to a drying step. This drying step dehydrates the gel. The dehydrated gel is customarily referred to as a "film".

The next step in this procedure entails the visualization of the fixed lipoproteins in the film. Staining techniques are a commonly employed visualization methodology.

After the staining operation, destaining is the next step which is performed on the film. Various solutions and solvents capable of use in destaining methodologies have been reported.

The films are again dried via one of numerous known techniques.

The stained lipoproteins in the dried films can then be evaluated by known techniques, e.g., densitometry and integration.

Densitometers are well known devices which scan a sample and provide an output signal or graphical display indicative of the optical density, transmittance, absorption or the like of the scanned sample.

One well known use of the densitometer is to scan a sample of blood which has been prepared by the electrophoresis process. As noted above, electrophoresis of blood samples separates various proteins in the blood from each other. Each of these separated proteins exhibit light absorption characteristics based upon the density of each protein and the light absorption patterns are graphically displayed by the densitometer to indicate the presence and quantity of each of these proteins via a series of peaks and valleys as shown, for example, in FIG. 1.

There has been much discussion in the literature concerning the nature of the lipid bands migrating in the alpha electrophoretic zone (6-9, 11, 12, 14-16). While some authors feel that there are two lipoprotein bands migrating in the alpha zone (12), designated as alpha lipoprotein and pre-alpha lipoprotein, the majority of authors feel the faster moving alpha band does not contain a lipoprotein but is instead serum albumin containing bound free fatty acids (11, 12, 16). With this latter position in mind, one problem in the use of known prior art gel formulations for the electrophoretic separation of lipoproteins is that the alpha lipoprotein band 106, as shown in FIG. 1, does not separate from the free fatty acid albumin band 108. As a result, when the electrophoretic gel is stained for detection of lipoproteins by lipid dyes, the free fatty acid albumin band 108, which is also stained by lipid dyes, interferes with the evaluation of the alpha lipoprotein band 106.

Accordingly, it would be very desirable to have an electrophoretic gel for use in the separation of lipoprotein which is capable of separating the alpha lipoprotein band 106 from the free fatty acid albumin band 108.

SUMMARY OF THE INVENTION

In accordance with the present invention there is provided an improved electrophoretic gel which, when used in an electrophoretic process for the separating chylomicrons, beta lipoproteins, pre-beta lipoproteins, and alpha lipoproteins into distinct bands, enables the separation of the alpha lipoprotein band from the free fatty acid albumin band. More particularly, the electrophoretic gel comprises (a) a matrix selected from the group consisting of polysaccharides and derivatives thereof, (b) a buffer having a buffering capacity in an alkaline pH range, and (c) a poly(oxyethylene)-poly(oxypropylene)-poly(oxyethylene) block copolymer in an amount such that the alpha lipoprotein band is substantially separated from the free fatty acid albumin band when the gel is employed in an electrophoretic procedure for the separation of the above lipoproteins.

In addition, the present invention also encompasses an improved electrophoretic technique. The electrophoretic technique comprises the steps of (a) applying a sample to be assayed to the above electrophoretic gel, (b) electrophoresing the electrophoretic gel, (c) immobilizing the lipoproteins in the electrophoresed gel, and (d) evaluating the immobilized lipoproteins.

Still other features and attendant advantages of the present invention will become apparent to those skilled in the art from a reading of the following detailed description of the preferred embodiments.

DESCRIPTION OF THE PREFERRED EMBODIMENTS

Figure 1:
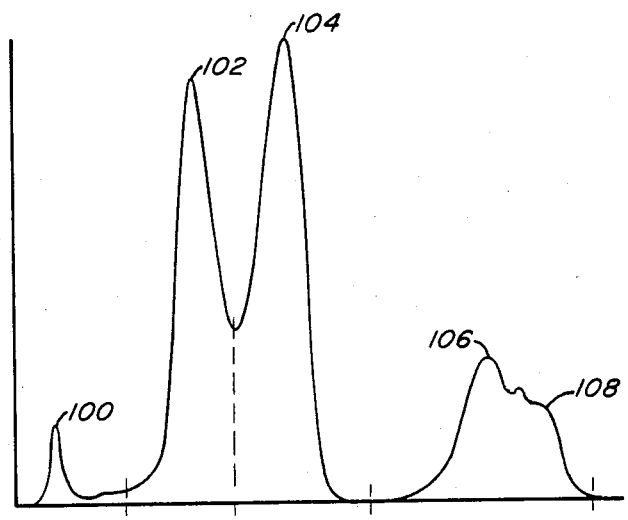
FIG. 1 is a scan of a lipoprotein pattern showing an overlap of the alpha lipoprotein band 106 and the free fatty acid albumin band 108 obtained using the prior art electrophoretic gel of Example 1.
Figure 2:
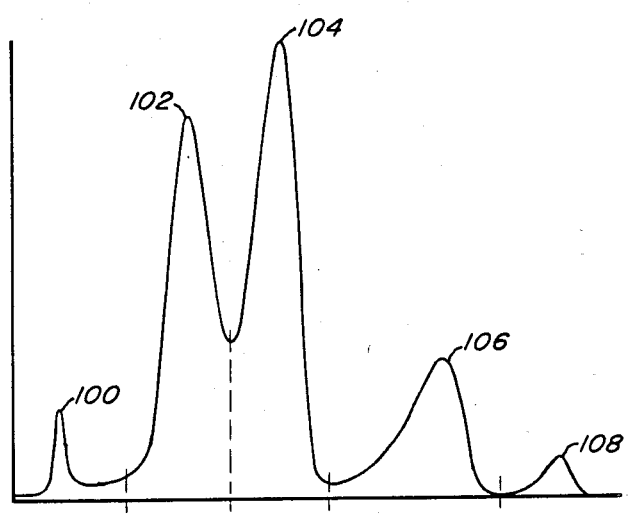
FIG. 2 is a scan of a lipoprotein pattern showing separation of the alpha lipoprotein band 106 from the free fatty acid albumin band 108 obtained using the electrophoretic gel of Example 2.
Figure 3:
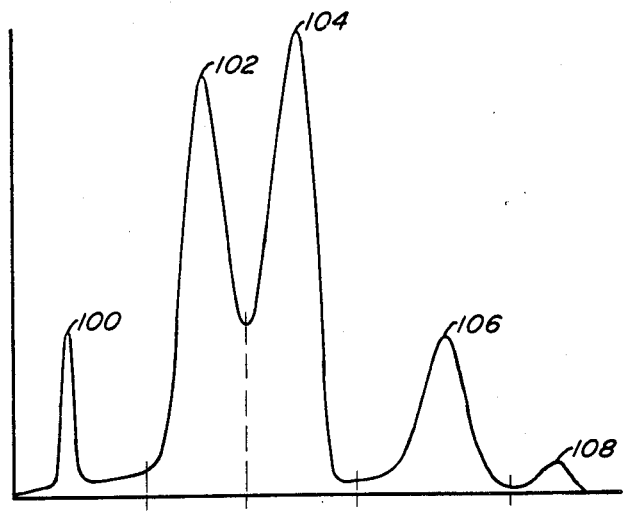
FIG. 3 is a scan of a lipoprotein pattern showing a separation of the alpha lipoprotein band 106 from the free fatty acid albumin band 108 obtained using the electrophoretic gel of Example 3.
Figure 4:
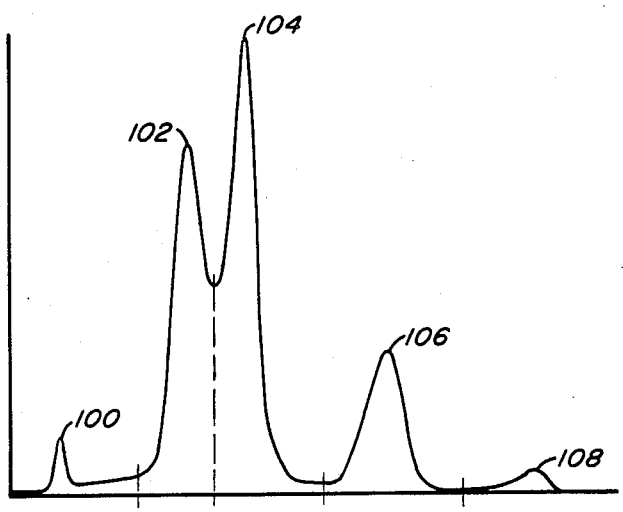
FIG. 4 is a scan of a lipoprotein pattern showing a separation of the alpha lipoprotein band 106 from the free fatty acid albumin band 108 obtained using the electrophoretic gel of Example 4.
Figure 5:
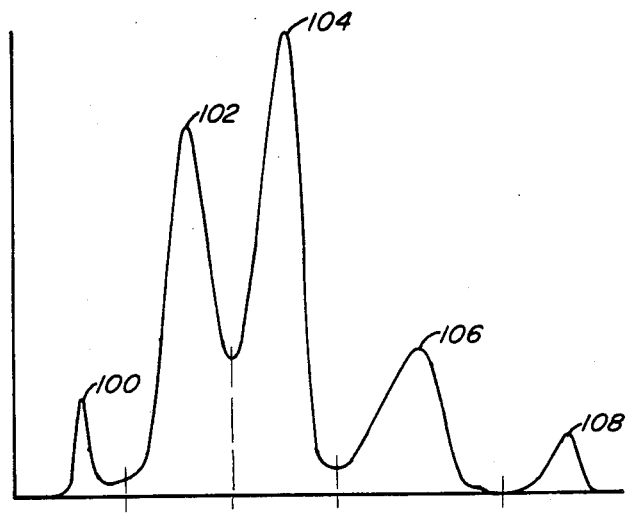
FIG. 5 is a scan of a lipoprotein pattern showing a separation of the alpha lipoprotein band 106 from the free fatty acid albumin band 108 obtained using the electrophoretic gel of Example 5.
Figure 6:
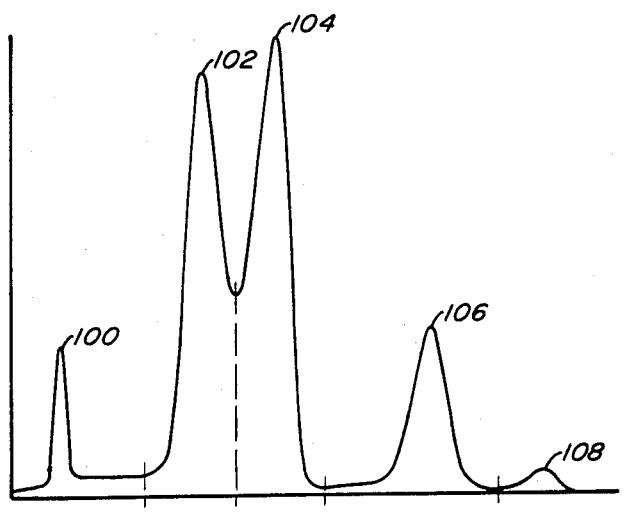
FIG. 6 is a scan of a lipoprotein pattern showing a separation of the alpha lipoprotein band 106 from the free fatty acid albumin band 108 obtained using the electrophoretic gel of Example 6.
Figure 7:
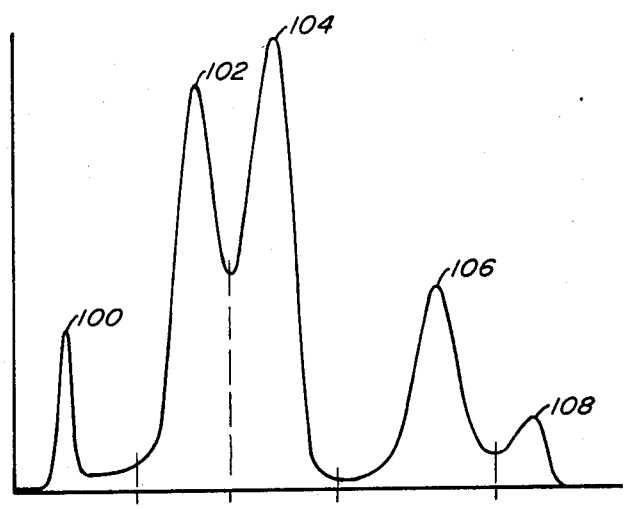
FIG. 7 is a scan of a lipoprotein pattern showing a separation of the alpha lipoprotein band 106 from the free fatty acid albumin band 108 obtained using the electrophoretic gel of Example 7.

The polysaccharide is preferably selected from the group consisting of agar, agarose and mixtures thereof. More preferably, the polysaccharide is selected from the group consisting of agarose and mixtures of agarose and agar. Optimally, the polysaccharide is agarose. The gel preferably comprises about 0.4 to about 1.2, more preferably about 0.5 to about 0.6, weight percent polysaccharide.

The buffer preferably has a buffering capacity in the pH range of about 7 to about 10, more preferably about 8 to about 9. Typical buffers include, but are not limited to, barbital, bicine, and tris buffers. The buffer of choice is barbital buffer having a pH of about 8.6.

Preferably, albumin is also present in the gel in an amount sufficient to improve the sharpness of the beta lipoprotein band. An effective amount of albumin can be from about 0.05 to about 1, preferably, about 0.1 to about 0.5, and more preferably about 0.2 to about 0.4 weight percent. The sources of albumin, include, but are not limited to, bovine.

The electrophoretic gel of the instant invention can also optionally contain a gel stabilizer. Typical gel stabilizers include, but are not limited to, alkylpolyols having 2-6 carbon atoms and 2-4 hydroxyl groups and mono- and disaccharides. Suitably alkyl polyols which can be used herein include, but are not limited to, ethylene glycol, propanediol, butanediol, and glycerol. Preferably, the alkyl polyol has 2-4 carbon atoms.

Suitable mono- and disaccharides include, but are not limited to, sorbitol and sucrose.

The gel stabilizer, when employed, should be present in an amount effective to reduce syneresis, i.e., the exudation of water from the gel during prolonged standing. Accordingly, the gel preferably comprises from about 3 to about 10 weight percent stabilizer. More preferably, the gel comprises from about 4 to about 6 weight percent stabilizer.

An antimicrobial agent can also optionally be incorporated into the electrophoretic gel of the instant invention. Typical antimicrobial agents include, but are not limited to, sodium azide, thimerosal, phenylmercuric acetate, and mixtures thereof. The amount of antimicrobial agent incorporated into the gel should be sufficient to inhibit the growth of microbial organisms. Such amount will vary with the particular antimicrobial agent employed.

The electrophoretic gel of the instant invention preferably comprises about 0.0001 to about 2 weight percent of the poly(oxyethylene)-poly(oxypropylene)-poly(oxyethylene) block copolymers, wherein the block copolymer has a molecular weight of about 1,000 to about 15,500. More preferably, the electrophoretic gel comprises about 0.001 to about 1 weight percent of the block copolymer having a molecular weight of about 3,000 to about 11,000 and comprising about 50 to about 80 weight percent poly(oxyethylene) and 20 to about 50 weight percent poly(oxypropylene).

The electrophoretic gel of the instant invention can be made via any method known to those skilled in the art. (1, 2, 4, 5, 8) For example, the gel solution can be prepared by dissolving the polysaccharide in water via heating the solution to a temperature of about 90° to about 100° C. The solution can then be cooled to about 50° to about 60° C. After the solution has been cooled, the other ingredients can be added.

The electrophoretic gel can be prepared by either standard molding or casting techniques. The gels can be stored at any convenient temperature, for example from about 2° to about 30° C., preferably from about 18° to about 26° C. It is preferred to store the electrophoretic gels in sealed, plastic trays until ready for use.

The electrophoretic gel can be used in any of the electrophoretic techniques for the separation of lipoproteins known to those skilled in the art. (1-3, 5-8, 19). For example, samples can be applied to the electrophoretic gels of the instant invention via any technique used in the prior art, e.g., via a microliter syringe. The electrophoretic gels can be electrophoresed at 100 volts (i.e., 9.5 volts per cm) for 30 minutes. The gels are next fixed, dried, stained, destained, dried, and evaluated.

By applying a sample to the electrophoretic gel of the instant invention and electrophoresing the gel, one achieves a greater differential in the relative electrophoretic migration rates of the alpha lipoprotein and free fatty acid albumin bands.

The following examples are provided for the purpose of further illustration only and are not intended to be limitations on the disclosed invention.

EXAMPLES 1-7

A. Preparation of Gel Solutions

To 80% of the calculated amount of water was added 0.6% w/w agarose. The solution was heated to between about 95° to about 100° C., with stirring, until the agarose dissolved. The agarose solution was then cooled to between about 50° to about 60° C. The remaining ingredients set forth in Table I were then added to the cooled solution, with stirring. Water was then added to the solution to bring the solution to its proper weight.

TABLE I

| | Example | | | | | | |
|---|---|---|---|---|---|---|---|
| | 1 | 2 | 3 | 4 | 5 | 6 | 7 |
| Ingredients | Prior Art | Present Invention | | | | | |
| Agarose, % w/w | 0.6 | 0.6 | 0.6 | 0.6 | 0.6 | 0.6 | 0.6 |
| Barbital Buffer, pH 8.6, % w/w | 1.0 | 1.0 | 1.0 | 1.0 | 1.0 | 1.0 | 1.0 |
| 30% Bovine Albumin, % w/w | 0.2 | 0.2 | 0.2 | 0.2 | 0.2 | 0.2 | 0.2 |
| 1,2-Propanediol, % w/w | 5.0 | 5.0 | 5.0 | 5.0 | 5.0 | 5.0 | 5.0 |
| Sodium Azide, % w/w | 0.1 | 0.1 | 0.1 | 0.1 | 0.1 | 0.1 | 0.1 |
| Thimerosal, % w/w | 0.01 | 0.01 | 0.01 | 0.01 | 0.01 | 0.01 | 0.01 |
| PEG-PPG Block Copolymer, % w/w | — | 0.005 | 0.05 | 0.01 | 0.70 | 0.01 | 0.02 |
| % PEG | — | 80 | 80 | 70 | 80 | 50 | 50 |
| ave. molecular wt. | — | 10,800 | 8,350 | 6,600 | 5,000 | 4,150 | 3,400 |
| Water | Q.S. to equal 100% by wt. | | | | | | |

B. Preparation of Gels

Gels were prepared by one of two methods. The first method entailed spreading the gel solution at about 50° to about 60° C. upon a PMC GelBond TM brand polyester film and allowing the solution to solidify into a gel.

The second method entailed injecting the gel solution at about 50° to about 60° C. into a mold containing a sheet of PMC GelBond TM brand polyester film. The injected solution was also allowed to solidify into a gel.

Gels prepared by both procedures were stored in sealed foil bags at about 20° to about 26° C.

C. Electrophoresis Methodology

1. Blot gel surface with filter paper to remove excess moisture.
2. Apply samples via template method (samples 24 hours old).
3. Electrophorese at 100 volts (9.5 v/cm) for 30 minutes without cooling at room temperature (24°-26° C.).
4. Fix gel in acid solution and dry gel to a film.
5. Stain with a lipid stain.
6. Destain.
7. Dry
8. Scan with a densitometer at 600 nm.

Graphs obtained as a result of the densitometric reading of lipoprotein separations obtained via the gels of Examples 1-7 are set forth in FIGS. 1-7, respectively, wherein the following numerical designations are employed.

TABLE II

| Numerical Designation | Classification |
|---|---|
| 100 | Chylomicron band |
| 102 | Beta lipoprotein band |
| 104 | Pre-beta lipoprotein band |
| 106 | Alpha lipoprotein band |
| 108 | Free fatty acid albumin band |

As shown in FIG. 1, a lipoprotein electrophoretic procedure performed with the prior art gel yields a substantial overlap between the alpha lipoprotein band 106 and the free fatty acid albumin band 108. In contrast, a lipoprotein electrophoretic procedure performed with a gel within the scope of this invention, as demonstrated in Examples 2-7, yields a marked improved separation between the alpha lipoprotein band 106 and the free fatty acid albumin band 108. This improved electrophoretic separation substantially eliminates the interference previously encountered in the evaluation of the alpha lipoprotein band 106.

Based on this disclosure, many other modifications and ramifications will naturally suggest themselves to those skilled in the art. These are intended to be comprehended as within the scope of this invention.

BIBLIOGRAPHY

1. Cawley, *Electrophoresis and Immunoelectrophoresis*, Little, Brown and Company, Boston, Mass. (1966).
2. *CRC Handbook of Electrophoresis*, Volumes I-IV, CRC Press, Inc., Boca Raton, Fla. (I and II—1980, III and IV—1983).
3. Houtsmuller, *Agarose-Gel-Electrophoresis of Lipoproteins*, Charles C. Thomas, Publisher, The Netherlands (1969).
4. *Agarose Monograph*, FMC Corporation, Marine Colloids Division, Rockland, Maine (1982).
5. Noble, *J. of Lipid Research*, 9: 693-700 (1968).
6. Papadopoulos et al., *Analytical Biochemistry*, 30: 421-6 (1969).
7. Zollner et al., *Z. Klin. Chem. v. Klin. Biochem*, 7: 525-9 (1969).
8. Dyerberg et al., *Clinica Chimica Acta*, 28: 203-8 (1970).
9. Kostner et al., *Hoppe-Seyleris Z. Physiol. Chem.*, 352: 1440-4 (1971).
10. Papadopoulos et al., *Clin. Chem.*, 17(5): 427-9 (1971).
11. Dyerberg et al., *Clin. Chim. Acta*, 33: 458-61 (1971).
12. Messerschmidt et al., *Clin. Chim. Acta*, 36: 51-60 (1972).
13. Phillips et al., *Clin. Chim. Acta*, 49: 153-60 (1973).
14. Dyerberg et al., *Clin. Chim. Acta*, 43: 283-4 (1973).
15. Wille, *Clin. Chim. Acta*, 57: 63-9 (1974).
16. Phillips et al., *Clin. Chim. Acta*, 50: 425-30 (1974).
17. Papadopoulos, *Clin. Chem.*, 21(13): 2004-8 (1975).
18. Papadopoulos, *Clin. Chem.*, 25(11): 1885-7 (1979).
19. Cawley, *Workshop Manual on Electrophoresis and Immunoelectrophoresis*, Commission on Continuing Education, Council on Clinical Chemistry, American Society of Clinical Pathologies (1966).

The embodiments of the invention in which an exclusive property or privilege is claimed are defined as follows:

1. An electrophoretic gel comprising a matrix selected from the group consisting of polysaccharides and derivatives thereof, a buffer having a buffering capacity in an alkaline pH range, and an effective amount of a poly(oxyethylene)-poly(oxypropylene)-poly(oxyethylene) block copolymer.

2. The gel of claim 1 comprising about 0.0001 to about 2 weight percent of said block copolymer, said block copolymer having a molecular weight of about 1,000 to about 15,500.

3. The gel of claim 1 comprising about 0.001 to about 1 weight percent of said block copolymer, said block copolymer having a molecular weight of about 3,000 to about 11,000 and comprising about 50 to about 80 weight percent poly(oxyethylene) and about 20 to about 50 weight percent poly(oxypropylene).

4. The gel of claim 1 further comprising from about 0.5 to about 1 weight percent albumin.

5. The gel of claim 1 wherein:
   (a) said buffer has a buffering capacity in the pH range of 7 to 10; and
   (b) said gel comprises about 0.0001 to about 2 weight percent of said block copolymer, said block copolymer having a molecular weight of about 1,000 to about 15,500.

6. The gel of claim 1 comprising about 0.0001 to about 2 weight percent of said block copolymer.

7. The gel of claim 6 comprising about 0.001 to about 1 weight percent of said block copolymer.

8. The gel of claim 1 wherein said block copolymer has a molecular weight of about 1,000 to about 15,500.

9. The gel of claim 8 wherein said block copolymer has a molecular weight of about 3,000 to about 11,000.

10. An electrophoretic gel comprising a matrix selected from the group consisting of agar, agarose, and mixtures thereof, a buffer having a buffering capacity in an alkaline pH range, and an effective amount of a poly(oxyethylene)-poly(oxypropylene)-poly(oxyethylene) block copolymer.

11. The gel of claim 10 comprising about 0.0001 to about 2 weight percent of said block copolymer.

12. The gel of claim 11 comprising about 0.001 to about 1 weight percent of said block copolymer.

13. The gel of claim 10 wherein said block copolymer has a molecular weight of about 1,000 to about 15,500.

14. The gel of claim 13 wherein said block copolymer has a molecular weight of about 3,000 to about 11,000.

15. The gel of claim 10 wherein said block copolymer comprises about 50 to about 80 weight percent poly(oxyethylene) and about 20 to about 50 weight poly(oxypropylene).

16. The gel of claim 10 comprising about 0.0001 to about 2 weight percent of said block copolymer, said block copolymer having a molecular weight of about 1,000 to about 15,500.

17. The gel of claim 10 comprising about 0.001 to about 1 weight percent of said block copolymer, said block copolymer having a molecular weight of about 3,000 to about 11,000 and comprising about 50 to about 80 weight percent poly(oxyethylene) and about 20 to about 50 weight percent poly(oxypropylene).

18. The gel of claim 10 wherein said matrix is selected from the group consisting of agarose and mixtures of agarose and agar.

19. The gel of claim 10 further comprising from about 0.5 to about 1 weight percent albumin.

20. The gel of claim 10 wherein:
   (a) said buffer has a buffering capacity in the pH range of 7 to 10; and
   (b) said gel comprises about 0.0001 to about 2 weight percent of said block copolymer, said block copolymer having a molecular weight of about 1,000 to about 15,500.

* * * * *

UNITED STATES PATENT AND TRADEMARK OFFICE
CERTIFICATE OF CORRECTION

PATENT NO. : 4,696,958

DATED : September 29, 1987

INVENTOR(S) : William A. Gurske

It is certified that error appears in the above-identified patent and that said Letters Patent is hereby corrected as shown below:

Column 8, line 13, between "weight" and "poly(oxy-" the word "percent" should be inserted.

Signed and Sealed this

Nineteenth Day of January, 1988

Attest:

DONALD J. QUIGG

*Attesting Officer*     *Commissioner of Patents and Trademarks*